United States Patent
Liu

(10) Patent No.: US 11,432,758 B2
(45) Date of Patent: Sep. 6, 2022

(54) LEFT AND RIGHT BRAIN RECOGNITION METHOD AND DEVICE

(71) Applicant: BEIJING ZHIGU TECH CO., LTD., Beijing (CN)

(72) Inventor: Hao Liu, Beijing (CN)

(73) Assignee: BEIJING ZHIGU TECH CO., LTD., Beijing (CN)

( * ) Notice: Subject to any disclaimer, the term of this patent is extended or adjusted under 35 U.S.C. 154(b) by 538 days.

(21) Appl. No.: 15/506,492

(22) PCT Filed: Aug. 26, 2015

(86) PCT No.: PCT/CN2015/088103
§ 371 (c)(1),
(2) Date: Feb. 24, 2017

(87) PCT Pub. No.: WO2016/029849
PCT Pub. Date: Mar. 3, 2016

(65) Prior Publication Data
US 2017/0245778 A1    Aug. 31, 2017

(30) Foreign Application Priority Data

Aug. 27, 2014    (CN) .......................... 201410427998.3

(51) Int. Cl.
*A61B 5/00*    (2006.01)
*A61B 5/16*    (2006.01)
(Continued)

(52) U.S. Cl.
CPC .............. *A61B 5/38* (2021.01); *A61B 5/0006* (2013.01); *A61B 5/165* (2013.01); *A61B 5/291* (2021.01);
(Continued)

(58) Field of Classification Search
None
See application file for complete search history.

(56) References Cited

U.S. PATENT DOCUMENTS

2006/0116600 A1 *   6/2006   Vesely ................. A61B 5/0482
                                                              600/559
2008/0221472 A1     9/2008   Lee et al.
(Continued)

FOREIGN PATENT DOCUMENTS

CN       102091376 A1    6/2011
CN       103054587 A     4/2013
(Continued)

OTHER PUBLICATIONS

Cecchin, T., Ranta, R., Koessler, L., Caspary, O., Vespignani, H., & Maillard, L. (2010). Seizure lateralization in scalp EEG using Hjorth parameters. Clinical Neurophysiology, 121(3), 290-300. doi:10.1016/j.clinph.2009.10.033 (Year: 2010).*

(Continued)

*Primary Examiner* — Allen Porter
*Assistant Examiner* — Samuel C Kim
(74) *Attorney, Agent, or Firm* — Sheppard Mullin Richter & Hampton LLP

(57) ABSTRACT

The present application provides a left and right brain recognition method and device, and relates to the field of wearable devices. The method comprises: in response to that a user listens to an audio content meeting a predetermined condition, acquiring first brain electrical information of a first hemisphere of the user; and recognizing that the first hemisphere is a left brain or a right brain according to the first brain electrical information and reference information. The method and the device provide a left and right brain (Continued)

recognition method, facilitate a device that the user wears to perform automatic setting according to a recognition result, and enhance user experience.

19 Claims, 8 Drawing Sheets

(51) Int. Cl.
  *A61B 5/291* (2021.01)
  *A61B 5/316* (2021.01)
  *A61B 5/374* (2021.01)
  *A61B 5/38* (2021.01)

(52) U.S. Cl.
  CPC .............. *A61B 5/316* (2021.01); *A61B 5/374* (2021.01); *A61B 5/6803* (2013.01); *A61B 5/4064* (2013.01)

(56) References Cited

U.S. PATENT DOCUMENTS

| | | | |
|---|---|---|---|
| 2009/0214060 A1 | 8/2009 | Chuang et al. | |
| 2011/0130675 A1 | 6/2011 | Bibian et al. | |
| 2015/0320332 A1* | 11/2015 | Lee | A61B 5/0048 600/545 |

FOREIGN PATENT DOCUMENTS

| | | |
|---|---|---|
| CN | 104161512 A | 11/2014 |
| JP | 2003-325467 A | 11/2003 |
| WO | 2013/162295 A1 | 10/2013 |

OTHER PUBLICATIONS

Trainor, Laurel. (2001). Frontal brain electrical activity (EEG) distinguishes valence and intensity of musical emotions. Cognition & Emotion—Cognition Emotion. 15. 487-500. 10.1080/02699930126048. (Year: 2001).*

PlatinumGMAT (2011). Adding & Subtracting Inequalities. Retrieved online on May 1, 2019 from <www.platinumgmat.com/gmat_study_guide/inequalities_adding> (Year: 2011).*

Baier, G., Hermann, T., & Stephani, U. (2007). Event-based sonification of EEG rhythms in real time. Clinical Neurophysiology, 118(6), 1377-1386. doi: 10.1016/j.clinph.2007.01.025 (Year: 2007).*

Hinterberger, T., Orchestral Sonification of Brain Signals and its Application to Brain-Computer Interfaces and Performing Arts. Proceedings of the 2nd International Workshop on Interactive Sonification, York, UK, Feb. 3, 2007. (Year: 2007).*

Wei, J. et al., "Unsymmetrical Response Features of Left and Right Brain to Signals from Left and Right Visual Fields at Different Cognitive Levels", Space Medicine & Medical Engineering, Jun. 2000, vol. 13 No. 3, Institute of Space Medico-Engineering, Beijing China, pp. 157-161.

Schmidt, L.A. et al., "Frontal brain electrical activity (EEG) distinguishes valence and intensity of musical emotions", Cognition and Emotion, 2001, vol. 15, No. 4, p. 487-500.

International Search Report and Written Opinion for Application No. PCT/CN2015/088103, dated Nov. 3, 2015, 8 pages.

* cited by examiner

LEFT AND RIGHT BRAIN RECOGNITION METHOD AND DEVICE

RELATED APPLICATION

The present application is a 371 National Phase of International Patent Application No. PCT/CN2015/088103, filed on Aug. 26, 2015, which claims the benefit of priority to Chinese Patent Application No. 201410427998.3, filed on Aug. 27, 2014, and entitled "Left and Right Brain Recognition Method and Device," each of which is incorporated herein by reference in its entirety.

TECHNICAL FIELD

The present application relates to the field of wearable technologies, and more particularly, to left and/or right brain recognition.

BACKGROUND

With the development of electronic devices, especially wearable devices, people more and more tend to make the electronic devices have certain self-recognition capability, so as to save user time and improve user experience.

Headphones are one kind of earphones that people usually use and generally comprise a left earphone and a right earphone respectively connected to a left channel and a right channel of an audio source. When a user wears earphones, if the user wears the left earphone and the right earphone incorrectly, listening experience of the user will be reduced. Therefore, in order to facilitate the user to distinguish the left and right earphones, "left" and "right" are usually marked on the left and right earphones respectively. Such a distinguishing manner evidently does not conform to modern fast-paced way of life, resulting in a waste of user time.

SUMMARY

An objective of the various embodiments of the present application is to provide a left and right brain recognition methods and devices.

According to one aspect of at least one embodiment of the present application, a left and right brain recognition method is provided, the method comprising:

in response to that a user listens to an audio content meeting a predetermined condition, acquiring first brain electrical information of a first hemisphere of the user; and recognizing that the first hemisphere is a left brain or a right brain according to the first brain electrical information and reference information.

According to one aspect of at least one embodiment of the present application, a left and right brain recognition device is provided, the device comprising:

a first acquisition module, configured to, in response to that a user listens to an audio content meeting a predetermined condition, acquire first brain electrical information of a first hemisphere of the user; and a recognition module, configured to recognize that the first hemisphere is a left brain or a right brain according to the first brain electrical information and reference information.

The left and right brain recognition method and device of the embodiments of the present application, in response to that a user listens to an audio content meeting a predetermined condition, acquire first brain electrical information of a first hemisphere of the user, and then recognize that the first hemisphere is a left brain or a right brain according to the first brain electrical information and reference information, so as to provide a left and right brain recognition method and device, thereby facilitating a device that the user wears to perform automatic setting according to a recognition result, and enhancing user experience.

DETAILED DESCRIPTION

Exemplary embodiments of the present application are described in further detail below with reference to the accompanying drawings and embodiments. The following embodiments are intended to describe the present application, but not to limit the scope of the present application.

It should be understood by those skilled in the art that, in the embodiments of the present application, the value of the serial number of each step described below does not mean an execution sequence, and the execution sequence of each step should be determined according to the function and internal logic thereof, and should not be any limitation to the implementation procedure of the embodiments of the present application.

FIG. 1 is a flowchart of the left and right brain recognition method according to one embodiment of the present application; the method may be implemented on, for example, a left and right brain recognition device. As shown in FIG. 1, the method comprises:

S120: in response to that a user listens to an audio content meeting a predetermined condition, acquiring first brain electrical information of a first hemisphere of the user; and S140: recognizing that the first hemisphere is a left brain or a right brain according to the first brain electrical information and reference information.

The method according to the embodiment of the present application, in response to that a user listens to an audio content meeting a predetermined condition, acquires first brain electrical information of a first hemisphere of the user, and then recognizes that the first hemisphere is a left brain or a right brain according to the first brain electrical information and reference information, so as to provide a left and right brain recognition method and device, thereby facilitating a device that the user wears to perform automatic setting according to a recognition result, and enhancing user experience.

Functions of steps S120 and S140 are described in detail below in combination with specific implementations.

S120: In response to that a user listens to an audio content meeting a predetermined condition, acquire first brain electrical information of a first hemisphere of the user.

The audio content may be, for example, at least one sound information such as a piece of music, broadcast, comic dialogue, chirping, sound of running water, and sound of waves.

The predetermined condition comprises enabling the user to be happy or the user to be sad, that is to say, the audio content meeting a predetermined condition is an audio content that makes the user happy or an audio content that makes the user sad.

The first hemisphere may be a left brain or a right brain of the user. The human brain can be divided into a left hemisphere and a right hemisphere, the left hemisphere is the left brain, and the right hemisphere is the right brain. In the present application, the left brain or the right brain is called a hemisphere.

Figure 1A:
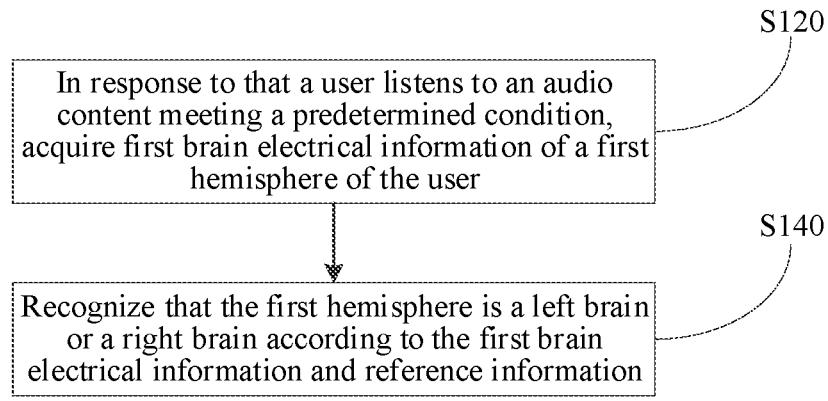
FIG. 1A is a flowchart of the left and right brain recognition method according to one embodiment of the present application.
Figure 1B:
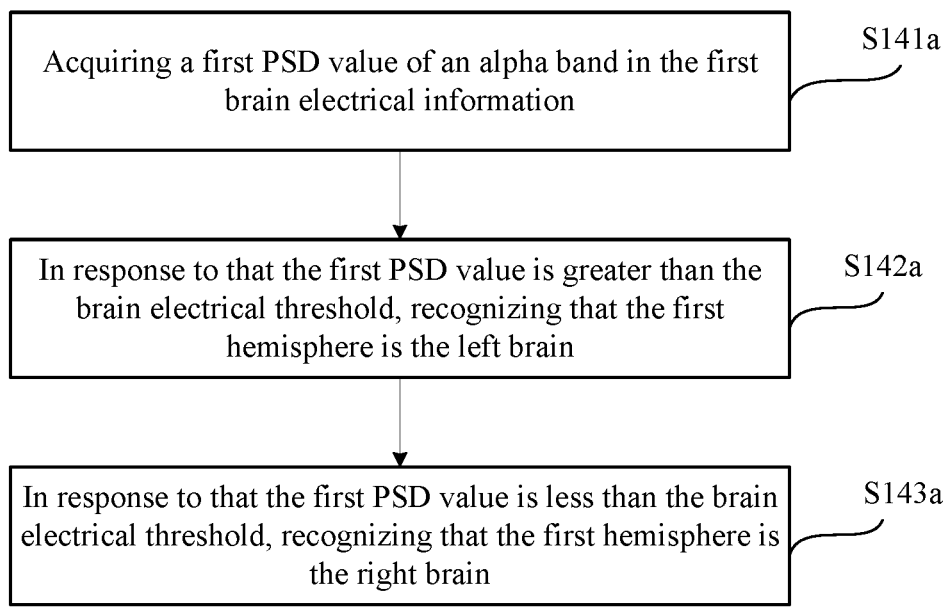
FIG. 1B is a flowchart illustrating operation S140 in FIG. 1A in the event that the audio content meets a first predetermined condition when the reference information is a brain electrical threshold determined according to left brain electrical information and right brain electrical information of the user, according to one embodiment of the present application.
Figure 1C:
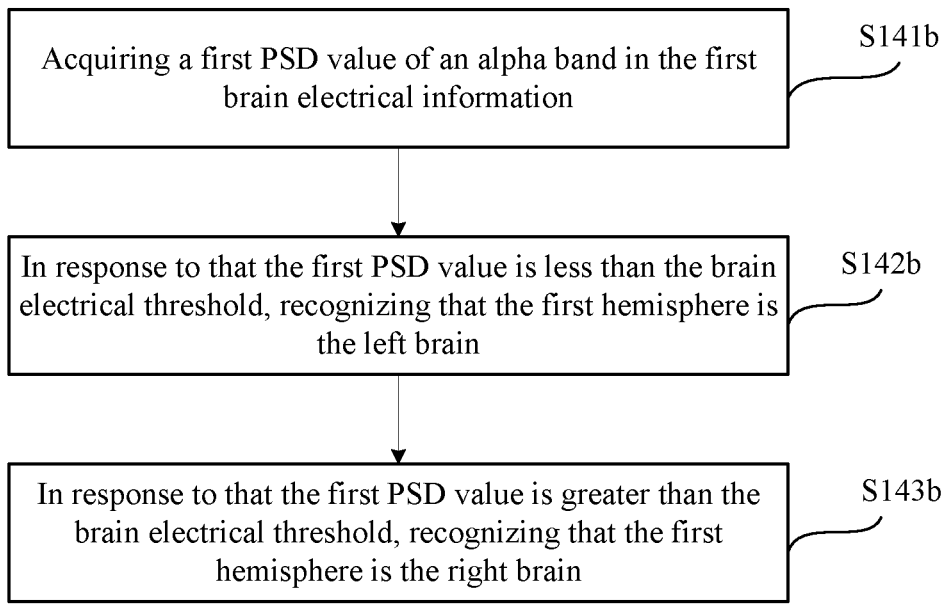
FIG. 1C is a flowchart illustrating operation S140 in FIG. 1A in the event that the audio content meets a second predetermined condition when the reference information is a brain electrical threshold determined according to left brain electrical information and right brain electrical information of the user, according to one embodiment of the present application.
Figure 1D:
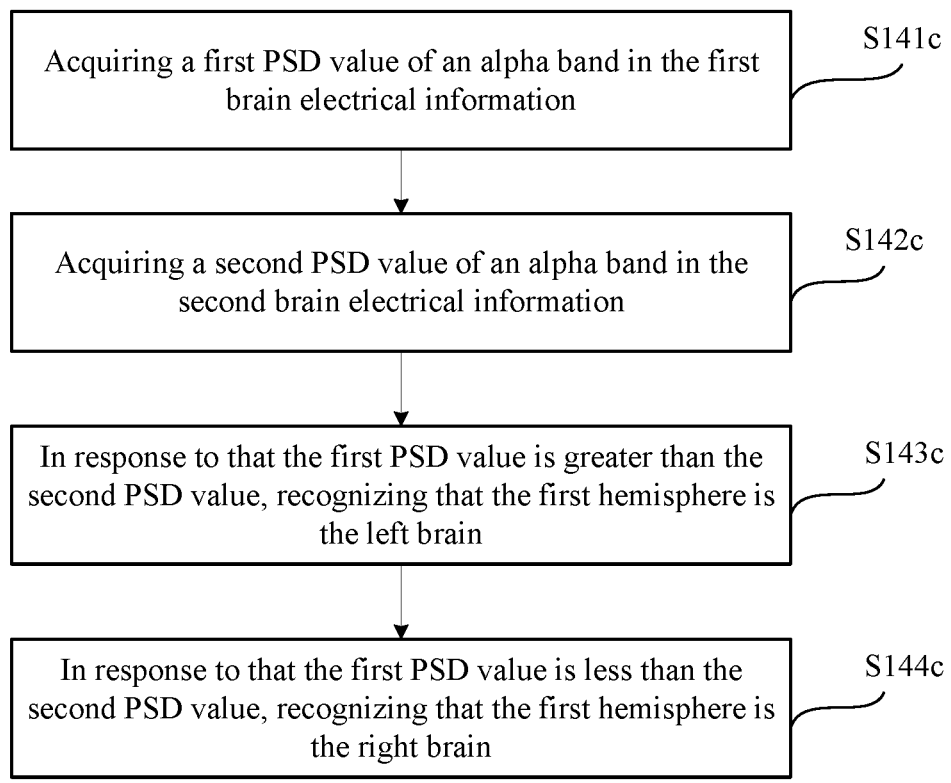
FIG. 1D is a flowchart illustrating operation S140 in FIG. 1A in the event that the audio content meets a first predetermined condition when the reference information is second brain electrical information of a second hemisphere of the user, according to one embodiment of the present application.
Figure 1E:
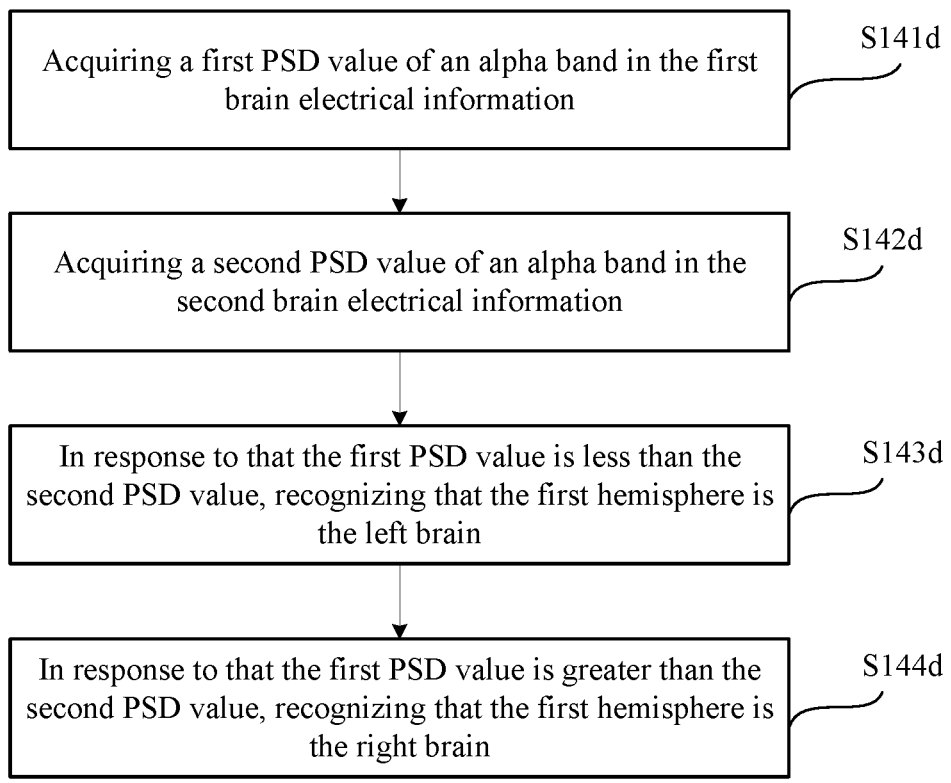
FIG. 1E is a flowchart illustrating operation S140 in FIG. 1A in the event that the audio content meets a second predetermined condition when the reference information is second brain electrical information of a second hemisphere of the user, according to one embodiment of the present application.
Figure 2:
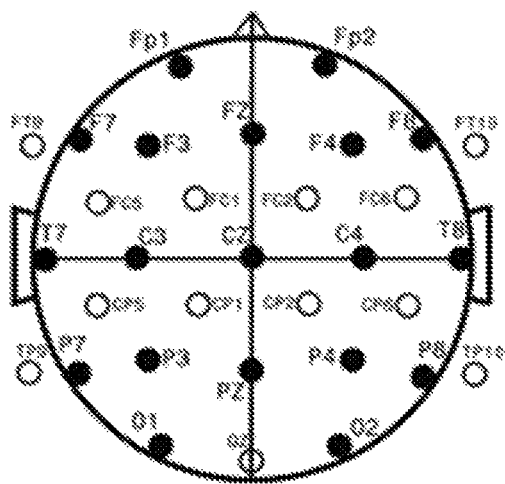
FIG. 2 is a schematic diagram of a universal EEG electrode placement system.

The first brain electrical information may be, for example, an electroencephalograhy (EEG) signal of the first hemisphere, which can be detected and acquired through an EEG sensor in contact with the cortex. FIG. 2 is a schematic diagram of a universal EEG electrode placement system, the filled circle (e.g., F3) and the empty circle (e.g., CP1) in FIG. 2 represent positions where the electrode can be placed, in the method of the present application, in order to ensure that the acquired brain electrical information is accurate and reliable, for example, brain electrical information of the user's left brain can be acquired at the position of C3 in FIG. 2, and brain electrical information of the user's right brain can be acquired at the position of C4 in FIG. 2.

S140: Recognize that the first hemisphere is a left brain or a right brain according to the first brain electrical information and reference information.

The inventor has found in the research process that an EEG signal is a current signal generated by a potential difference between cerebral cortical cell groups outside cells of the cerebral cortex when the brain is active. It records wave changes when the brain is active, and is a reflection of electrophysiological activities of neural cells on pallium or surface of head. According to a hemispheric specialization hypothesis, when people are in a pleasant (Positively valenced) emotional state, a Power Spectral Density (PSD) value of an alpha band (i.e., 8-12 Hz) of the left brain electrical information is greater than a PSD value of an alpha band of the right brain electrical information; on the contrary, when people are in a sad (Negatively valenced) emotional state, the PSD value of the alpha band of the left brain electrical information is less than the PSD value of the alpha band of the right brain electrical information. In addition, the inventor has also found that, for example, an audio content such as a piece of happy music can be used to arouse the user's joyful emotion, and for example, an audio content such as a piece of sad music can be used to arouse the user's sad emotion. The present application achieves recognition on left and right brains based on the foregoing principle.

In one embodiment, the reference information is a brain electrical threshold determined according to left brain electrical information and right brain electrical information of the user.

In the event that the audio content meets a first predetermined condition, that is, the audio content is an audio content that can arouse the user's joyful emotion, step S140 may comprise (with reference to FIG. 1B):

S141a: acquiring a first PSD value of an alpha band in the first brain electrical information;

S142a: in response to that the first PSD value is greater than the brain electrical threshold, recognizing that the first hemisphere is the left brain; and S143a: in response to that the first PSD value is less than the brain electrical threshold, recognizing that the first hemisphere is the right brain.

For example, in the event that the audio content is an audio content that can arouse the user's joyful emotion, the reference information may be the brain electrical threshold determined according to a left PSD value of an alpha band in the left brain electrical information of the user and a right PSD value of an alpha band in the right brain electrical information; suppose that the left PSD value falls within a first left interval ($L_{min1}, L_{max1}$), and suppose that the right PSD value falls within a first right interval ($R_{min1}, R_{max1}$), it can be determined that the brain electrical threshold is M1, and $L_{min1}>M1>R_{max1}$. That is to say, the brain electrical threshold M1 is a value between the first left interval and the first right interval.

Therefore, if the first PSD value is greater than the brain electrical threshold M1, it is considered that the first PSD value falls within the first left interval, and the first hemisphere is the left brain; if the first PSD value is less than the brain electrical threshold M1, it is considered that the first PSD value falls within the first right interval, and the first hemisphere is the right brain.

In the event that the audio content meets a second predetermined condition, that is, the audio content is an audio content that can arouse the user's sad emotion, step S140 may comprise (with reference to FIG. 1C):

S141*b*: acquiring a first PSD value of an alpha band in the first brain electrical information;

S142*b*: in response to that the first PSD value is less than the brain electrical threshold, recognizing that the first hemisphere is the left brain; and S143*b*: in response to that the first PSD value is greater than the brain electrical threshold, recognizing that the first hemisphere is the right brain.

For example, in the event that the audio content is an audio content that can arouse the user's sad emotion, the reference information may be the brain electrical threshold determined according to a left PSD value of an alpha band in the left brain electrical information of the user and a right PSD value of an alpha band in the right brain electrical information; suppose that the left PSD value falls within a second left interval ($L_{min2}$, $L_{max2}$), and suppose that the right PSD value falls within a second right interval ($R_{min2}$, $R_{max2}$), it can be determined that the brain electrical threshold is M2, and $R_{min2}>M2>L_{max2}$. That is to say, the brain electrical threshold M2 is a value between the second left interval and the second right interval.

Therefore, if the first PSD value is less than the brain electrical threshold M2, it is considered that the first PSD value falls within the second left interval, and the first hemisphere is the left brain; if the first PSD value is greater than the brain electrical threshold M2, it is considered that the first PSD value falls within the second right interval, and the first hemisphere is the right brain.

It should be noted that, in the embodiment, the reference information needs to be determined according to left brain electrical information and right brain electrical information of the user. Therefore, it is necessary to pre-acquire left brain electrical information and right brain electrical information of the user in a corresponding predetermined condition, for example, left brain electrical information and right brain electrical information of the user are acquired respectively while a piece of pleasant music is played for the user, so as to complete the training process.

In another embodiment, the reference information is second brain electrical information of a second hemisphere of the user.

In the event that the audio content meets a first predetermined condition, that is, the audio content is an audio content that can arouse the user's joyful emotion, step S140 may comprise (with reference to FIG. 1D):

S141*c*: acquiring a first PSD value of an alpha band in the first brain electrical information;

S142*c*: acquiring a second PSD value of an alpha band in the second brain electrical information;

S143*c*: in response to that the first PSD value is greater than the second PSD value, recognizing that the first hemisphere is the left brain; and S144*c*: in response to that the first PSD value is less than the second PSD value, recognizing that the first hemisphere is the right brain.

In the event that the audio content meets a second predetermined condition, that is, the audio content is an audio content that can arouse the user's sad emotion, step S140 may comprise (with reference to FIG. 1E):

S141*d*: acquiring a first PSD value of an alpha band in the first brain electrical information;

S142*d*: acquiring a second PSD value of an alpha band in the second brain electrical information;

S143*d*: in response to that the first PSD value is less than the second PSD value, recognizing that the first hemisphere is the left brain; and S144*d*: in response to that the first PSD value is greater than the second PSD value, recognizing that the first hemisphere is the right brain.

In the embodiment, the user does not need to perform pre-training, for example, first brain electrical information of the first hemisphere and second brain electrical information of the second hemisphere of the user can be acquired respectively in the event that the audio content meets a first predetermined condition, then magnitudes of a first PSD value of the first brain electrical information and a second PSD value of the second brain electrical information are compared, and then the first hemisphere is recognized.

In the present application, the audio content meeting a first predetermined condition, that is, the audio content that can arouse the user's pleasant emotion can be acquired through experiments, for example, a candidate song is broadcast to and listened to by 100 audience, then every audience feeds back his/her own emotion, and if more than 90 audience feeds back that they feel good, the song is recorded as a song meeting the first predetermined condition; the operations are repeated for a plurality of candidate songs, and a song library meeting a first predetermined condition can be obtained. Similarly, a song library meeting a second predetermined condition can be obtained.

In addition, the audio content may also be directly selected from an existing International Affective Digitized Sounds (IADS) library, the IADS library comprises a plurality of audio contents with labels, and the labels are configured to indicate that the audio contents can arouse the user's pleasant emotion or sad emotion.

It should be noted that, because music per se is configured to express emotion, and for the audience may present no language barrier, music is easier to be accepted by most users, and thus more suitable as the audio content of the present application.

In addition, in order to ensure the recognition result, that is, ensure that the recognition result is obtained in the event that the audio content effectively arouses the user's emotion, and a play duration of the audio content is greater than a predetermined duration, for example, 10 s.

Figure 3:
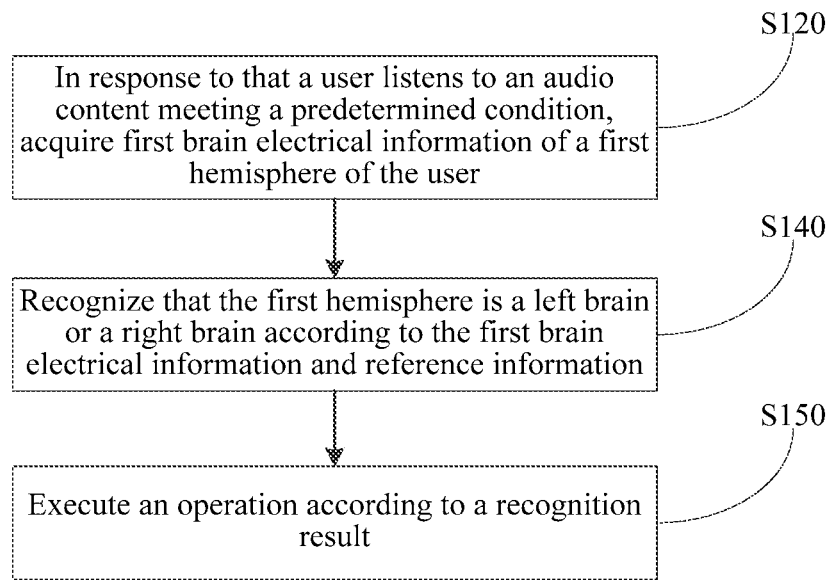
FIG. 3 is a flowchart of the left and right brain recognition method according to one embodiment of the present application.

As shown FIG. 3, in one embodiment, the method further comprises:

S150: executing an operation according to a recognition result.

By taking that the recognition result is configured to configure channels as an example, channels of earphones corresponding to the first hemisphere and/or the second hemisphere can be configured according to the recognition result. For example, suppose that the recognition result shows that the first hemisphere is the left brain, the channel of the earphone corresponding to the first hemisphere can be configured as a left channel, and certainly, the channel of the earphone corresponding to the second hemisphere can be configured as a right channel at about the same time. By taking that the earphones are headphones as an example, the earphone corresponding to the first hemisphere is closer to an earphone receiver of the first hemisphere than the second hemisphere.

In addition, some other operations may also be executed according to the recognition result, for example, some researchers studying the left and right brains may often need to acquire related information of the left and right brains, the left and right brains can be automatically recognized by using the method of the present application, so as to automatically recognize that the acquired information is information corresponding to the left brain or the right brain, and reduce steps set by the staff. Alternatively, the recognition result may also serve as input information in a user game process.

In addition, the embodiment of the present application further provides a computer readable medium, comprising computer readable instructions that perform the following operations when being executed: executing the operations of steps S120 and S140 of the method in the embodiment shown in FIG. 1.

To sum up, the method according to the embodiments of the present application can recognize that the first hemisphere is a left brain or a right brain according to the first brain electrical information and reference information, and execute corresponding operations such as setting channels of earphones according to a recognition result, thereby reducing setting operations of the user, and enhancing user experience.

Figure 4:
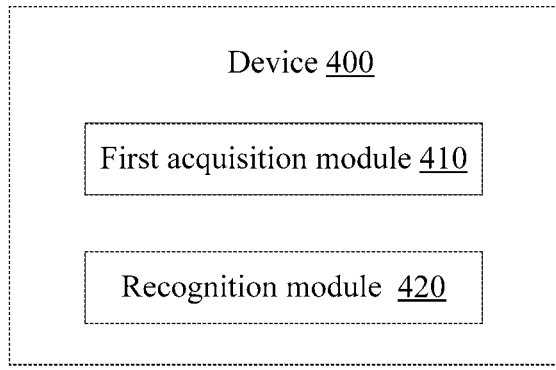
FIG. 4 is a schematic diagram of a modular structure of the left and right brain recognition device according to one embodiment of the present application.

FIG. 4 is a schematic diagram of a modular structure of the left and right brain recognition device according to one embodiment of the present application; the left and right brain recognition device may be set, as a functional module, in a wearable device such as a headphone, and certainly, may also be used by a user as a separate wearable device. As shown in FIG. 4, the device 400 may comprise:
    a first acquisition module 410, configured to, in response to that a user listens to an audio content meeting a predetermined condition, acquire first brain electrical information of a first hemisphere of the user; and
    a recognition module 420, configured to recognize that the first hemisphere is a left brain or a right brain according to the first brain electrical information and reference information.

The apparatus according to the embodiment of the present application, acquires first brain electrical information of a first hemisphere of the user, and then recognizes that the first hemisphere is a left brain or a right brain according to the first brain electrical information and reference information, so as to provide a left and right brain recognition device, thereby facilitating a device that the user wears to perform automatic setting according to a recognition result, and enhancing user experience.

Functions of the first acquisition module 410 and the recognition module 420 are described in detail below in combination with specific implementations.

A first acquisition module 410, configured to, in response to that a user listens to an audio content meeting a predetermined condition, acquire first brain electrical information of a first hemisphere of the user.

The audio content may be, for example, at least one sound information such as a piece of music, broadcast, comic dialogue, chirping, sound of running water, and sound of waves.

The predetermined condition comprises enabling the user to be happy or the user to be sad, that is to say, the audio content meeting a predetermined condition is an audio content that makes the user happy or an audio content that makes the user sad.

The first hemisphere may be a left brain or a right brain of the user. The human brain can be divided into a left hemisphere and a right hemisphere, the left hemisphere is the left brain, and the right hemisphere is the right brain. In the present application, the left brain or the right brain is called a hemisphere.

The first brain electrical information may be, for example, an EEG signal of the first hemisphere, which can be detected and acquired through an EEG sensor in contact with the cortex. As shown in FIG. 2, brain electrical information of the user's left brain can be acquired at the position of C3 in FIG. 2, and brain electrical information of the user's right brain can be acquired at the position of C4 in FIG. 2.

A recognition module 420, configured to recognize that the first hemisphere is a left brain or a right brain according to the first brain electrical information and reference information.

Figure 5:
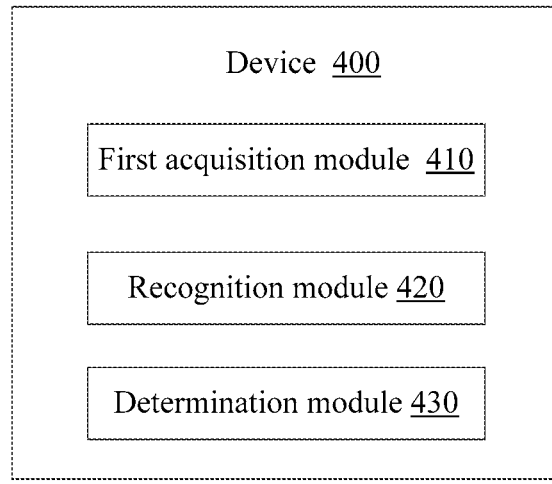
FIG. 5 is a schematic diagram of a modular structure of the left and right brain recognition device according to one embodiment of the present application.

As shown in FIG. 5, in one embodiment, the device 400 further comprises:
    a determination module 430, configured to determine a brain electrical threshold as the reference information according to left brain electrical information and right brain electrical information of the user.

Figure 6:
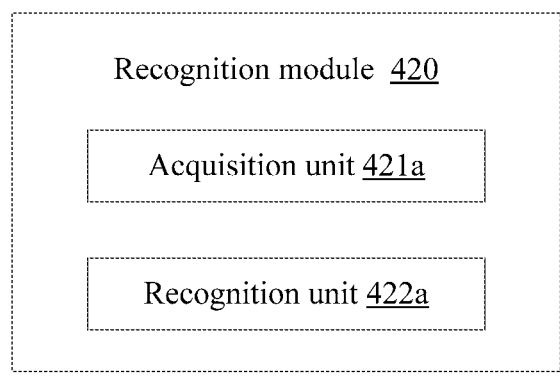
FIG. 6 is a schematic diagram of a modular structure of the recognition module according to one embodiment of the present application.

As shown in FIG. 6, in one embodiment, the audio content meets a first predetermined condition, that is, the audio content is an audio content that can arouse the user's joyful emotion, and the recognition module 420 comprises:
    an acquisition unit 421a, configured to acquire a first PSD value of an alpha band in the first brain electrical information; and
    a recognition unit 422a, configured to, in response to that the first PSD value is greater than the brain electrical threshold, recognize that the first hemisphere is the left brain; and
    in response to that the first PSD value is less than the brain electrical threshold, recognize that the first hemisphere is the right brain.

For example, in the event that the audio content is an audio content that can arouse the user's joyful emotion, the reference information may be the brain electrical threshold determined according to a left PSD value of an alpha band in the left brain electrical information of the user and a right PSD value of an alpha band in the right brain electrical information; suppose that the left PSD value falls within a first left interval ($L_{min1}, L_{max1}$), and suppose that the right PSD value falls within a first right interval ($R_{min1}, R_{max1}$), it can be determined that the brain electrical threshold is M1, and $L_{min1} > M1 > R_{max1}$. That is to say, the brain electrical threshold M1 is a value between the first left interval and the first right interval.

Therefore, if the first PSD value is greater than the brain electrical threshold M1, it is considered that the first PSD value falls within the first left interval, and the first hemisphere is the left brain; if the first PSD value is less than the brain electrical threshold M1, it is considered that the first PSD value falls within the first right interval, and the first hemisphere is the right brain.

Figure 7:
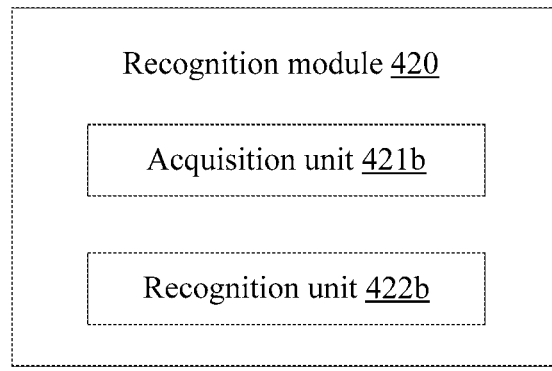
FIG. 7 is a schematic diagram of a modular structure of the recognition module according to one embodiment of the present application.

As shown in FIG. 7, in another embodiment, the audio content meets a second predetermined condition, that is, the audio content is an audio content that can arouse the user's sad emotion, and the recognition module 420 may comprise:
    an acquisition unit 421b, configured to acquire a first PSD value of an alpha band in the first brain electrical information; and a recognition unit 422b, configured to, in response to that the first PSD value is less than the brain electrical threshold, recognize that the first hemisphere is the left brain; and in response to that the first PSD value is greater than the brain electrical threshold, recognize that the first hemisphere is the right brain.

For example, in the event that the audio content is an audio content that can arouse the user's sad emotion, the reference information may be the brain electrical threshold determined according to a left PSD value of an alpha band in the left brain electrical information of the user and a right PSD value of an alpha band in the right brain electrical information; suppose that the left PSD value falls within a second left interval ($L_{min2}$, $L_{max2}$), and suppose that the right PSD value falls within a second right interval ($R_{min2}$, $R_{max2}$), it can be determined that the brain electrical threshold is M2, and $R_{min2} > M2 > L_{max2}$. That is to say, the brain electrical threshold M2 is a value between the second left interval and the second right interval.

Therefore, if the first PSD value is less than the brain electrical threshold M2, it is considered that the first PSD value falls within the second left interval, and the first hemisphere is the left brain; if the first PSD value is greater than the brain electrical threshold M2, it is considered that the first PSD value falls within the second right interval, and the first hemisphere is the right brain.

It should be noted that, in the embodiment, the reference information needs to be determined according to left brain electrical information and right brain electrical information of the user. Therefore, it is necessary to pre-acquire left brain electrical information and right brain electrical information of the user in a corresponding predetermined condition, for example, left brain electrical information and right brain electrical information of the user are acquired respectively while a piece of pleasant music is played for the user, so as to complete the training process.

Figure 8:
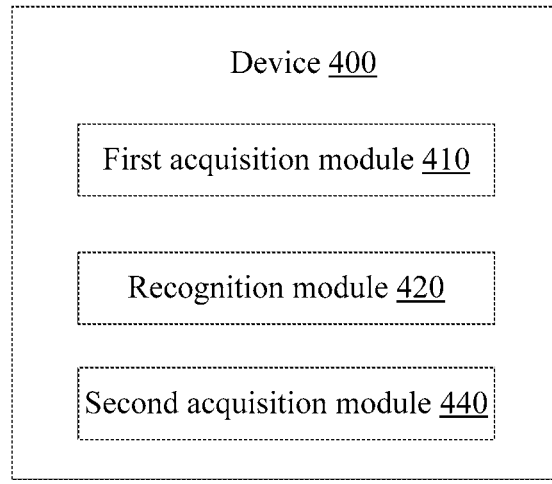
FIG. 8 is a schematic diagram of a modular structure of the left and right brain recognition device according to one embodiment of the present application.

As shown in FIG. 8, in one embodiment, the device 400 further comprises:

a second acquisition module 440, configured to acquire second brain electrical information of a second hemisphere of the user as the reference information.

Figure 9:
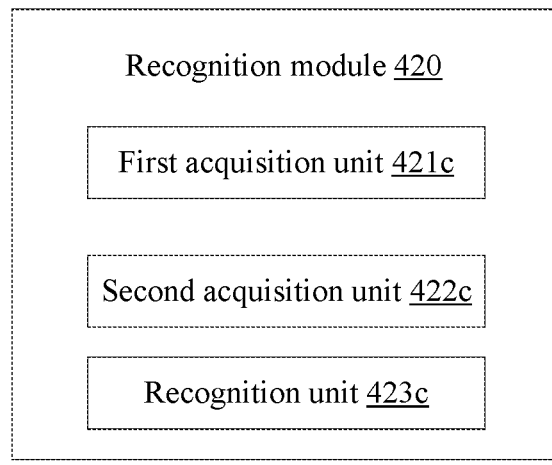
FIG. 9 is a schematic diagram of a modular structure of the recognition module according to one embodiment of the present application.

As shown in FIG. 9, in one embodiment, the audio content meets a first predetermined condition, that is, the audio content is an audio content that can arouse the user's joyful emotion, and the recognition module 420 comprises:

a first acquisition unit 421c, configured to acquire a first PSD value of an alpha band in the first brain electrical information;

a second acquisition unit 422c, configured to acquire a second PSD value of an alpha band in the second brain electrical information; and a recognition unit 423c, configured to, in response to that the first PSD value is greater than the second PSD value, recognize that the first hemisphere is the left brain; and in response to that the first PSD value is less than the second PSD value, recognize that the first hemisphere is the right brain.

Figure 10:
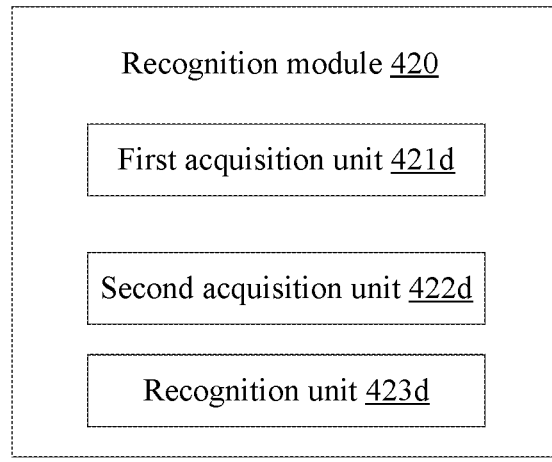
FIG. 10 is a schematic diagram of a modular structure of the recognition module according to one embodiment of the present application.

As shown in FIG. 10, in another embodiment, the audio content meets a second predetermined condition, that is, the audio content is an audio content that can arouse the user's sad emotion, and the recognition module 420 comprises:

a first acquisition unit 421d, configured to acquire a first PSD value of an alpha band in the first brain electrical information;

a second acquisition unit 422d, configured to acquire a second PSD value of an alpha band in the second brain electrical information; and a recognition unit 423d, configured to, in response to that the first PSD value is less than the second PSD value, recognize that the first hemisphere is the left brain; and in response to that the first PSD value is greater than the second PSD value, recognize that the first hemisphere is the right brain.

Figure 11:
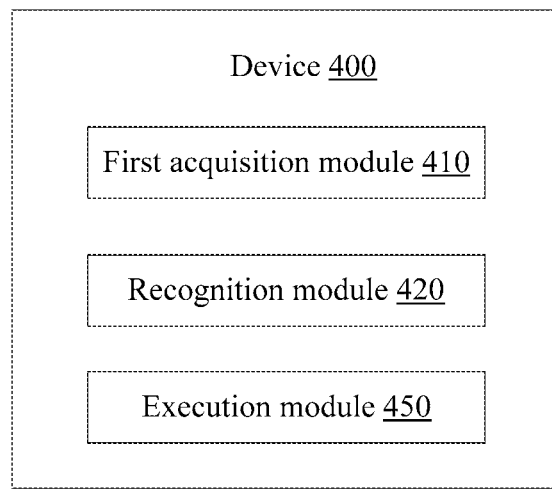
FIG. 11 is a schematic diagram of a modular structure of the left and right brain recognition device according to one embodiment of the present application.

As shown in FIG. 11, in one embodiment, the device 400 further comprises:

an execution module 450, configured to execute an operation according to a recognition result.

For example, in one embodiment, the execution module 450 is configured to configure channels of earphones corresponding to the first hemisphere and/or the second hemisphere according to the recognition result. In addition, some other operations may also be executed according to the recognition result, for example, some researchers studying the left and right brains may often need to acquire related information of the left and right brains, the left and right brains can be automatically recognized by using the method of the present application, so as to automatically recognize that the acquired information is information corresponding to the left brain or the right brain, and reduce steps set by the staff. Alternatively, the recognition result may also serve as input information in a user game process.

Figure 12:
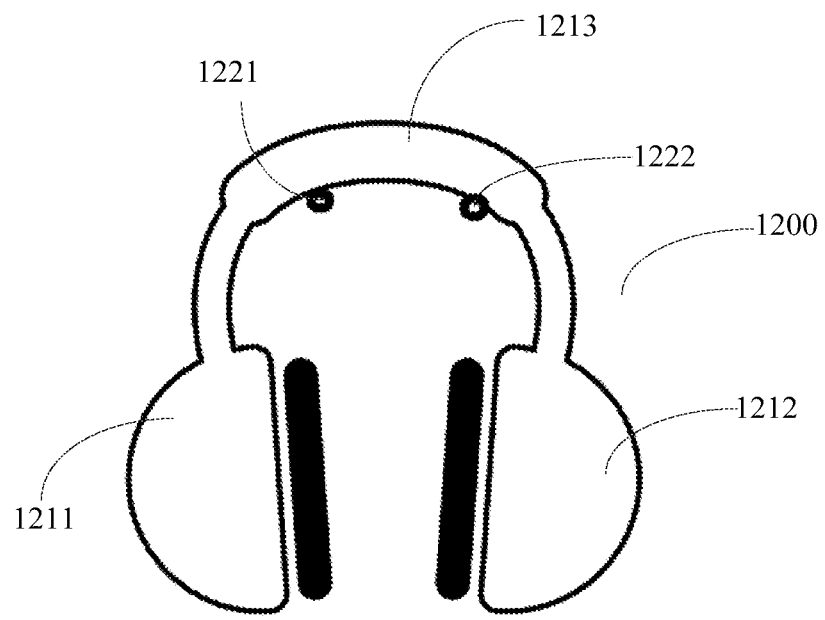
FIG. 12 is a schematic diagram of an application example of the left and right brain recognition device according to one embodiment of the present application.

FIG. 12 is a schematic diagram of an application example of the left and right brain recognition device according to one embodiment of the present application; in the application example, the left and right brain recognition device is a headphone 1200, comprising: a first receiver 1211, a second receiver 1212, a connecting portion 1213 connecting the first receiver 1211 and the second receiver 1212, a first EEG electrode 1221 and a second EEG electrode 1222 disposed on the connecting portion 1213. The first EEG electrode 1221 corresponds to the first receiver 1211, and the second EEG electrode 1222 corresponds to the second receiver 1212.

One application scenario of the left and right brain recognition method and device of the embodiments of the present application may be as follows: suppose that a user wears the headphone 1200 to prepare to listen to the radio, the headphone 1200, after monitoring that the user wears it, first plays a piece of pre-stored music that can make the user happy, during playback of the music, the first EEG electrode 1221 acquires brain electrical information of the first hemisphere in contact therewith, the second EEG electrode 1222 acquires brain electrical information of the second hemisphere in contact therewith, the first brain electrical information and the second brain electrical information are analyzed, and the left brain and the right brain of the user can be recognized. Suppose that the recognition result shows that the first hemisphere is the left brain, the channel of the first receiver 1211 is correspondingly configured as a left channel, and the channel of the second receiver 1212 is configured as a right channel.

Figure 13:
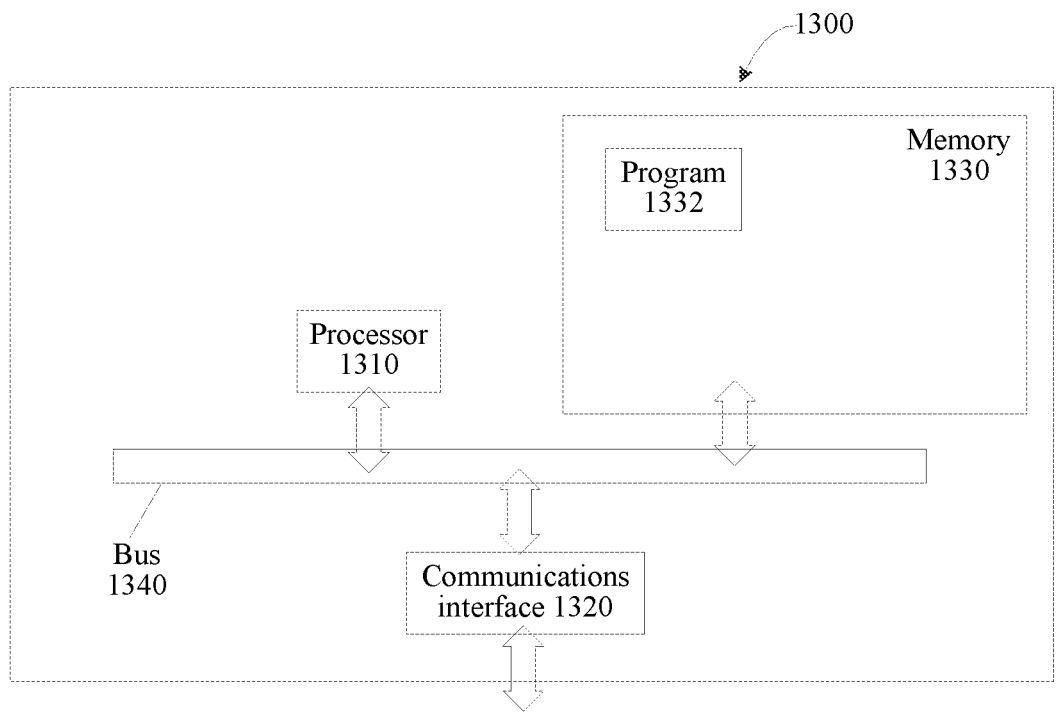
FIG. 13 is a schematic diagram of a hardware structure of the left and right brain recognition device according to one embodiment of the present application.

A hardware structure of the left and right brain recognition device according to another embodiment of the present application is as shown in FIG. 13. Exemplary embodiments of the present application do not limit specific implementation of the left and right brain recognition device; referring to FIG. 13, the apparatus 1300 may comprise:

a processor 1310, a communications interface 1320, a memory 1330, and a communications bus 1340.

The processor 1310, the communications interface 1320, and the memory 1330 communicate with each other by using the communications bus 1340.

The communications interface 1320 is configured to communicate with other network elements.

The processor 1310 is configured to execute a program 1332, and specifically can implement relevant steps in the embodiments shown in FIG. 1.

Specifically, the program 1332 may comprise a program code, where the program code comprises computer operation instructions.

The processor 1310 may be a central processing unit (CPU), or an application specific integrated circuit (ASIC), or may be configured as one or more integrated circuits that implement the embodiments of the present application.

The memory 1330 is configured to store the program 1332. The memory 1330 may comprise a high speed random access memory (RAM), and may also comprise a non-volatile memory such as at least one magnetic disk storage. The program 1332 may specifically execute the following steps:
  in response to that a user listens to an audio content meeting a predetermined condition, acquiring first brain electrical information of a first hemisphere of the user; and
  recognizing that the first hemisphere is a left brain or a right brain according to the first brain electrical information and reference information.

For the execution of the steps in the program 1332, please refer to the corresponding descriptions of corresponding steps or modules in the foregoing embodiments, which are not described herein again. It may be clearly understood by a person skilled in the art that, for the purpose of convenient and brief description, reference may be made to the description of corresponding procedures in the foregoing method embodiments for detailed working procedures of the foregoing devices and modules, and details are not described herein again.

It can be appreciated by a person of ordinary skill in the art that, exemplary units and method steps described with reference to the embodiments disclosed herein can be implemented by electronic hardware or a combination of computer software and electronic hardware. Whether these functions are executed by hardware or software depends on specific applications and design constraints of the technical solution. A person skilled in the art may use different methods to implement the described functions for each specific application, but such implementation should not be construed as a departure from the scope of the present application.

If the function is implemented in the form of a software functional unit and is sold or used as an independent product, the product can be stored in a computer-readable storage medium. Based on this understanding, the technical solution of the present application essentially, or the part that makes contributions to the art, or a part of the technical solution may be embodied in the form of a software product; the computer software product is stored in a storage medium and comprises several instructions for enabling a computer device (which may be a personal computer, a controller, a network device, or the like) to execute all or some of the steps of the method in the embodiments of the present application. The foregoing storage medium comprises a USB flash disk, a removable hard disk, a read-only memory (ROM), a random access memory (RAM), a diskette, an optical disk or any other medium that can store program codes.

The foregoing embodiments are only used to describe the present application, but not to limit the present application. A person of ordinary skill in the art can still make various alterations and modifications without departing from the spirit and scope of the present application; therefore, all equivalent technical solutions also fall within the scope of the present application, and the patent protection scope of the present application should be defined by the claims.

What is claimed is:

1. A left and right brain recognition method, comprising:
  receiving, by a left and right brain recognition device, an audio content;
  playing, by speakers of the left and right brain recognition device, the received audio content to a user;
  in response to that the user listens to the received audio content, acquiring, by a first electroencephalograhy (EEG) electrode of the left and right brain recognition device, first brain electrical information of a first hemisphere of the user, wherein the first EEG electrode is in contact with the first hemisphere, and the first brain electrical information comprises EEG signals of the first hemisphere;
  acquiring, by the left and right brain recognition device, a first Power Spectral Density (PSD) value of an alpha band in the first brain electrical information;
  recognizing, by the left and right brain recognition device, that the first hemisphere is a left brain or a right brain according to the first PSD value and reference information, and generating a recognition result indicating the first hemisphere being the left brain or the right brain; and
  automatically configuring, by the left and right brain recognition device, channels in a first speaker corresponding to the first hemisphere and/or channels in a second speaker corresponding to a second hemisphere of the user who listens to the audio content according to the recognition result.

2. The method of claim 1, wherein the audio content is a piece of music.

3. The method of claim 1, wherein a play duration of the audio content is greater than a predetermined duration.

4. The method of claim 1, wherein the reference information is a brain electrical threshold determined according to left brain electrical information and right brain electrical information of the user.

5. The method of claim 4, wherein
  the recognizing, by the left and right brain recognition device, that the first hemisphere is the left brain or the right brain according to the first PSD value and the reference information comprises:
    in response to that the first PSD value is greater than the brain electrical threshold, recognizing that the first hemisphere is the left brain; and
    in response to that the first PSD value is less than the brain electrical threshold, recognizing that the first hemisphere is the right brain.

6. The method of claim 4, wherein
  the recognizing, by the left and right brain recognition device, that the first hemisphere is the left brain or the right brain according to the first PSD value and the reference information comprises:
    in response to that the first PSD value is less than the brain electrical threshold, recognizing that the first hemisphere is the left brain; and
    in response to that the first PSD value is greater than the brain electrical threshold, recognizing that the first hemisphere is the right brain.

7. The method of claim 1, further comprising:
acquiring, by a second EEG electrode of the left and right brain recognition device, second brain electrical information of the second hemisphere of the user as the reference information, wherein the second brain electrical information comprises EEG signals of the second hemisphere, and the second EEG electrode is in contact with the second hemisphere.

8. The method of claim 7, wherein
the recognizing, by the left and right brain recognition device, that the first hemisphere is the left brain or the right brain according to the first PSD value first brain electrical information and the reference information comprises:
acquiring a second PSD value of an alpha band in the second brain electrical information;
in response to that the first PSD value is greater than the second PSD value, recognizing that the first hemisphere is the left brain; and
in response to that the first PSD value is less than the second PSD value, recognizing that the first hemisphere is the right brain.

9. The method of claim 7, wherein
the recognizing, by the left and right brain recognition device, that the first hemisphere is the left brain or the right brain according to the first PSD value and the reference information comprises:
acquiring a second PSD value of an alpha band in the second brain electrical information;
in response to that the first PSD value is less than the second PSD value, recognizing that the first hemisphere is the left brain; and
in response to that the first PSD value is greater than the second PSD value, recognizing that the first hemisphere is the right brain.

10. A non-transitory computer-readable storage medium storing instructions which, when executed by a processor, cause the processor to perform operations comprising:
receiving an audio content;
playing, through speakers, the received audio content to a user;
in response to that the user listens to the received audio content, acquiring, through a first electroencephalograhy (EEG) electrode, first brain electrical information of a first hemisphere of the user, wherein the first EEG electrode is in contact with the first hemisphere, and the first brain electrical information comprises EEG signals of the first hemisphere;
acquiring a first Power Spectral Density (PSD) value of an alpha band in the first brain electrical information;
recognizing that the first hemisphere is a left brain or a right brain according to the first PSD value and reference information, and generating a recognition result indicating the first hemisphere being the left brain or the right brain; and
automatically configuring channels in a first speaker corresponding to the first hemisphere and/or channels in a second speaker corresponding to a second hemisphere of the user who listens to the audio content according to the recognition result.

11. A left and right brain recognition device comprising a processor and a memory, the memory storing computer executable instructions, the processor being connected to the memory through a communication bus, wherein when the left and right brain recognition device operates, the processor executes the computer executable instructions stored in the memory, causing the left and right brain recognition device to execute operations comprising:
receiving an audio content;
playing, through speakers of the left and right brain recognition device, the received audio content to a user;
in response to that the user listens to the received audio content of, acquiring, through a first electroencephalograhy (EEG) electrode of the left and right brain recognition device, first brain electrical information of a first hemisphere of the user, wherein the first EEG electrode is in contact with the first hemisphere, and the first brain electrical information comprises EEG signals of the first hemisphere;
acquiring a first Power Spectral Density (PSD) value of an alpha band in the first brain electrical information;
recognizing that the first hemisphere is a left brain or a right brain according to the first PSD value and reference information, and generating a recognition result indicating the first hemisphere being the left brain or the right brain; and
automatically configuring channels of earphones in a first speaker corresponding to the first hemisphere and/or channels in a second speaker corresponding to a second hemisphere of the user who listens to the audio content according to the recognition result.

12. The device of claim 11, wherein the operations further comprise:
determining a brain electrical threshold as the reference information according to left brain electrical information and right brain electrical information of the user.

13. The device of claim 12, wherein the operations further comprise:
in response to that the first PSD value is greater than the brain electrical threshold, recognizing that the first hemisphere is the left brain; and
in response to that the first PSD value is less than the brain electrical threshold, recognizing that the first hemisphere is the right brain.

14. The device of claim 12, wherein the operations further comprise:
in response to that the first PSD value is less than the brain electrical threshold, recognizing that the first hemisphere is the left brain; and
in response to that the first PSD value is greater than the brain electrical threshold, recognizing that the first hemisphere is the right brain.

15. The device of claim 11, wherein the operations further comprise:
acquiring, through a second EEG electrode of the left and right brain recognition device, second brain electrical information of the second hemisphere of the user as the reference information, wherein the second EEG electrode is in contact with the second hemisphere, and the second brain electrical information comprises EEG signals of the second hemisphere.

16. The device of claim 15, wherein the operations further comprise:
acquiring a second PSD value of an alpha band in the second brain electrical information;
in response to that the first PSD value is greater than the second PSD value, recognizing that the first hemisphere is the left brain; and
in response to that the first PSD value is less than the second PSD value, recognizing that the first hemisphere is the right brain.

17. The device of claim 15, wherein the operations further comprise:
  acquiring a second PSD value of an alpha band in the second brain electrical information;
  in response to that the first PSD value is less than the second PSD value, recognizing that the first hemisphere is the left brain; and
  in response to that the first PSD value is greater than the second PSD value, recognizing that the first hemisphere is the right brain.

18. The device of claim 11, wherein the left and right brain recognition device is included in a headphone.

19. A left and right brain recognition device, comprising at least one executable instruction, which, in response to execution, causes a processor of the left and right brain recognition device to perform operations comprising:
  receiving an audio content;
  playing, through speakers of the left and right brain recognition device, the received audio content to a user;
  in response to that the user listens to the received audio content, acquiring, through a first electroencephalograhy (EEG) electrode of the left and right brain recognition device, first brain electrical information of a first hemisphere of the user, wherein the first EEG electrode is in contact with the first hemisphere, and the first brain electrical information comprises EEG signals of the first hemisphere;
  acquiring a first Power Spectral Density (PSD) value of an alpha band in the first brain electrical information;
  recognizing that the first hemisphere is a left brain or a right brain according to the first PSD value and reference information, and generating a recognition result indicating the first hemisphere being the left brain or the right brain; and
  automatically configuring channels of earphones in a first speaker corresponding to the first hemisphere and/or channels in a second speaker corresponding to a second hemisphere of the user who listens to the audio content according to the recognition result.

\* \* \* \* \*

UNITED STATES PATENT AND TRADEMARK OFFICE
CERTIFICATE OF CORRECTION

PATENT NO. : 11,432,758 B2
APPLICATION NO. : 15/506492
DATED : September 6, 2022
INVENTOR(S) : Hao Liu It is certified that error appears in the above-identified patent and that said Letters Patent is hereby corrected as shown below:

In the Claims

Claim 8, Column 13, Lines 12-14:
"the right brain according to the first PSD value first brain electrical information and the reference information comprises:" should read -- the right brain according to the first PSD value and the reference information comprises: --.

Claim 11, Column 14, Line 22:
"automatically configuring channels of earphones in a first speaker" should read -- automatically configuring channels in a first speaker --.

Claim 19, Column 16, Line 15:
"automatically configuring channels of earphones in a first speaker" should read -- automatically configuring channels in a first speaker --.

Signed and Sealed this
Ninth Day of January, 2024

Katherine Kelly Vidal
*Director of the United States Patent and Trademark Office*